United States Patent
Fabbri

(10) Patent No.: US 7,011,937 B2
(45) Date of Patent: Mar. 14, 2006

(54) METHOD AND SOLUTIONS FOR CRYOPRESERVING OOCYTES, ESPECIALLY FRESH HUMAN OOCYTES

(75) Inventor: Raffaella Fabbri, Prato (IT)

(73) Assignee: Medi-Cult A/S, Jyllinge (DK)

(*) Notice: Subject to any disclaimer, the term of this patent is extended or adjusted under 35 U.S.C. 154(b) by 363 days.

(21) Appl. No.: 10/251,624

(22) Filed: Sep. 20, 2002

(65) Prior Publication Data
US 2003/0077567 A1    Apr. 24, 2003

Related U.S. Application Data

(63) Continuation of application No. PCT/IT01/00139, filed on Mar. 20, 2001.

(30) Foreign Application Priority Data
Jun. 16, 2003  (IT)  ................ PI2000A000020

(51) Int. Cl.
*A01N 1/00*  (2006.01)
(52) U.S. Cl. ....................................... 435/1.3
(58) Field of Classification Search ................ 435/1.3
See application file for complete search history.

(56) References Cited

U.S. PATENT DOCUMENTS 5,985,538 A    11/1999  Stachecki .................. 435/1.1

OTHER PUBLICATIONS

De Boucaud et al., "The use of 1,2-propanediol for cryopreservation of reclacitrant seeds: the model case of Zea mays imbibed seeds", Cryo-Letters 9 (2) : 94-101 (1988).*

Otoi et al., "The Develpment of Immature Bovine Oocytes Cryopreserved by 1,2-Propanediol", J. Reproduction and Development 41 (4) : 361-366 (1995).*

Palasz, A. T. et al.: "Cryopreservation of Mammalian Embryos and Oocytes: Recent Advances"; Biotechnology Advances, vol. 14, No. 2, pp 127-149; 1996.

Otoi Takesbige et al.: "The Development of Immature Bovine Oocytes Cryopreserved by 1,2-Propanediol"; J. Reproduction and Development, pp 361-366; 1995. Abstract only.

Otoi T. et al.: "Cryopreservation of Mature Bovine Oocytes by Vitrification in Straws": Cryobiology, pp. 77-85; Aug. 1998, Abstract only.

J. -P. Renard et al., "Two-step freezing of two-cell rabbit embryos after partial dehydration at room temperature", J. Reprod. Fert. 71: 573-580 (1984).

* cited by examiner

*Primary Examiner*—Sandra E. Saucier
(74) *Attorney, Agent, or Firm*—Klein, O'Neill & Singh, LLP; Howard J. Klein

(57) ABSTRACT

In a method for cryopreserving fresh human oocytes, freezing and thawing solutions are used, which solutions include 1,2 propanediol (PROH) and sucrose at a concentration of at least 0.3M. The oocytes are exposed for 13–15 minutes to a solution including 1.5M PROH and 0.3M sucrose before starting the freezing process.

8 Claims, No Drawings

METHOD AND SOLUTIONS FOR CRYOPRESERVING OOCYTES, ESPECIALLY FRESH HUMAN OOCYTES

CROSS REFERENCE TO RELATED APPLICATION

This application is a Continuation of co-pending International Application No. PCT/IT01/00139; filed 20 Mar. 2001.

TECHNICAL FIELD

This invention relates to an improved method for cryopreserving oocytes, especially fresh human oocytes. This invention also relates to solutions particularly suitable for cryopreservation of oocytes, especially fresh human oocytes.

BACKGROUND ART

It is well known that cryopreservation of unfertilised human ooccytes is a technique which offers several advantages, especially whenever oocytes are to be preserved of patients who are at risk of ovarian hyperstimulation and can not transfer embryos during the in vitro fertilization treatment. However cryopreservation of oocytes, especially of fresh human oocytes, has run into greater technical difficulties than preservation of male gametes or embryos because of oocytes cytological peculiarity.

The low number of births from human cryopreserved oocytes, reported in literature, shows the technical difficulties of cryopreserving oocytes. Up to now researches carried out on oocytes cryopreservation provide congesting results regarding the more suitable and less damaging methods for maintaining cellular integrity and for getting a higher rate of viable oocytes.

As yet, a definitive protocol for cryopreserving human oocytes has not been established and the number of oocytes utilised up to now is still too low to determine a definitive methodology to be applied.

Human oocytes survival rate in cryopreservation depends, as well as on oocytes size, also on cryoprotectant used (composition, concentration and exposure time) and on freezing/thawing rate.

In the cryopreservation process, oocytes size is a very important parameter affecting the survival rate because the large quantity of water in ooplasm causes intracellular ice formation during the freezing, process: intracellular ice is one of the main responsible factors for intracellular structure damages.

Oocytes cryopreservation protocols usually include the following steps:
a) initially exposing the oocytes to a solution including a permeating cryoprotectant (e.g. 1,2-propanediol (PROH)), which aim is to reduce to a minimum intracellular structure damages caused by water crystallization;
b) subsequently exposing for a time of 2–5 min. the oocytes to a so-called loading solution including a mixture of a permeating cryoprotectant and a non permeating cryoprotectant (e.g. sucrose) to increase oocytes dehydration;
c) slowly cooling to −150° C.;
d) storing in liquid nitrogen (−196° C.);
e) thawing
f) diluting ad removing the cryoprotectants by exposure to so-called thawing solutions and returning to the physiological environment for further manipulations.

Cryoprotectants benefits are related to
I) their concentration,
II) exposure times,
III) the temperature at which they are added to oocytes.

Known methods for cryopreserving oocytes provide for using loading/thawing solutions including sucrose at a concentration of 0.1M or 0.2M.

DISCLOSURE OF INVENTION

In a method for cryopreserving oocytes, according to the present invention, it is provided for using loading/thawing solutions including sucrose at a concentration of 0.3M or greater.

In face, it has been surprisingly noticed that the presence of sucrose at a concentration of 0.3M or greater outside highly membrane highly increases cell dehydration/rehydration with an improvement of cryopreserved oocytes survival rate.

Furthermore, in a particular embodiment of the invention, the present method provides for exposing oocytes to a loading solution including at least 0.3M sucrose for a time of 15 min before starting the freezing process.

In this latter case, a morphological analysis, effected by an inverted microscope, has shown an oocyte cytoplasmatic volume reduction of about 30% with further dehydration; this also reduces the possibility of intracellular ice formation.

BEST MODE FOR CARRYING OUT THE INVENTION

The essential phases of a process, according to the present invention, for cryopreserving fresh human oocytes are described hereinafter.

The following solutions are used in the freezing process:
a PBS solution (Dulbecco's Phosphate Buffered Saline Solution w/o sodium bicarbonate);
an equilibration solution (1.5M PROH);
a loading solution (1.5M PROH+0.3M sucrose);
a SSS solution (Synthetic Serum Substitute)

The composition of the above solutions is as follows:
PBS solution
8 ml PBS
Equilibration solution (1.5M PROH)
6.79 ml PBS
1.21 ml PROH (1,2-propanediol)
Loading solution (1.5M PROH+0.3M sucrose)
6.79 ml PBS
1.21 ml PROH
1.128 gr sucrose These solutions arc used in a slow freezing program. The solutions are prepared, mixed, filtered and conserved at +4° C. It is better to maintain the solutions at room temperature for 15 min before using.

When the above described solutions are ready, a Petri dish is prepared with 2.1 ml of PBS solution+0.9 ml SSS (Synthetic Serum Substitute). In this solution all the oocytes are washed from their culture medium before transferring in the equilibration solution. Then a suitable dish provided with a plurality of wells is prepared: some of the wells contain 0.350 ml of equilibration solution (1.5M PROH)+0.150 ml of SSS (Synthetic Serum Substitute). In this solution 1 or 2 oocytes/well are transferred and maintained for 10 min before transferring in loading solution.

The others wells contain 0.350 ml of loading solution (1.5M PROH+0.3M sucrose)+0.150 ml of SSS (Synthetic Serum Substitute). The oocytes (taken from the equilibration solution) are transferred in the loading solution and rapidly loaded in plastic straws. Afterwards the straws are placed in a programmable freezer, e.g. a Kryo 10 series III (Planer Kryo 10/1.7 GB).

According to a particularly advantageous embodiment of the present method, before starting the freezing program the oocytes are Exposed to the loading solution (including sucrose at a concentration of at least 0.3M for 13–15 min and preferably for about 15 min.

Then a slow freezing method is applied to the oocytes as follows. The initial chamber temperature is 20° C. Then the temperature is slowly (2° C./min) reduced to −7° C. at which temperature ice nucleation is manually induced. After a hold time of 10 min at −7° C., the straws are cooled slowly (0.3° C./min) to −30° C. and then rapidly (50° C./min) to −150° C. After 10–12 min of stabilisation temperature, the straws are transferred into liquid nitrogen tanks and stored until thawing.

The following solutions are used in the thawing process:
a mother solution 1.0M PROH composed of
  14.35 ml PBS
  1.65 ml PROH
and utilized to prepares
  A) 1.0M PROH solution+0.3M sucrose, composed of
    8 ml of mother solution (1.0M PROH)
    1.128 gr sucrose
  B) 0.5M PROH solution+0.39 sucrose, composed of
    4 ml of mother solution (1.0M PROH)
    4 ml PBS
    1.128 gr sucrose.
The following solutions arc also used:
  C) 0.3M sucrose solution, composed of:
    8 ml PBS
    1.128 gr sucrose
  D) PBS solution composed of:
    8 ml PBS
  E) SSS solution (Synthetic Serum Substitute)

These solutions are utilized in a rapid thawing program. The solutions are prepared, mixed, filtered and conserved at +4° C. It is better to maintain the solutions at room temperature for 15 min before using.

To thaw, the straws are initially air-warned for 30 sec and then immersed in a 30° C. water bath for 40 sec until all traces of ice have disappeared Then, for each straw, a four wells dish is prepared for removing cryoprotectant by stepwise dilution of PROH in the thawing solutions:

More particularly, the first well contains 0.350 ml of solution A (1.0M PROH solution+0.3M sucrose)+0.150 ml of solution E SSS (Synthetic Serum Substitute). The content of the straw is expelled in this solution and the oocytes are equilibrated for 5 min at room temperature.

The second well contains 0.350 ml of solution B (0.5M PROH solution+0.3M sucrose)+0.150 ml SSS (Synthetic Serum Substitute). The oocytes, taken from the first well, are transferred to this solution and maintained for additional 5 min at room temperature.

The third well contains 0.350 ml of solution C (0.3M sucrose solution)+0.150 ml of SSS solution (Synthetic Serum Substitute). The oocytes, taken from the second well, are transferred to this solution and maintained for 10 min at room temperature.

The fourth well contains 0.350 ml of solution D (PBS solution)+0.150 ml of SSS solution (Synthetic Serum Substitute) The oocytes, taken from the third well, are transferred to this solution and maintained for 10 min at room temperature and for additional 10 min at 37° C.

Finally the oocytes can be transformed to a conventional culture medium before insemination.

Experimental data have shown a very high survival rate (92%) of fresh human oocytes cryopreserved with loading/thawing solutions including sucrose at a concentration of 0.3M. A higher survival rate is also observed when the oocytes are exposed to the loading solution for 13–15 min instead of 2–5 min.

What is claimed is:

1. A method for cryopreserving human oocytes comprising the steps of:
   exposing the ooccytes to a first solution comprising a permeating cryoprotectant that comprises 1,2 propanediol,
   exposing the ooccytes to a second solution comprising a permeating cryoprotectant that comprises 1,2 propanediol and a non-permeating cryoprotectant that comprises sucrose at a concentration of at least 0.3M,
   freezing the oocytes immersed in said second solution,
   storing the frozen oocytes in liquid nitrogen,
   thawing the oocytes, and
   diluting and removing the cryoprotectants by exposure to one or more thawing solutions.

2. The method of claim 1, characterized in that said thawing solutions comprise one or more solutions including sucrose at a concentration of 0.3M or greater.

3. The method of claim 2, characterized in that said thawing solutions comprise sucrose at a concentration of between 0.3M to 0.5M.

4. The method of claim 3, characterized in that said thawing solutions comprise sucrose at a concentration of 0.3M.

5. The method of claim 4, characterized in tat said thawing solutions comprise a solution (A) 1.0M PROH+0.3M sucrose, a solution (B) 0.5M PROH+0.3M sucrose, a solution (C) 0.3M sucrose, and a solution (D) Dulbecco's Phosphate Buffered Solution, and that said step of diluting and removing the cryoprotectants comprises the subsequent exposure of oocytes to solutions (A), (B), (C) and (D).

6. The method of claim 1, characterized in that said permeating cryoprotectant is 1,2-propanediol (PROH) at a concentration of 1.5M.

7. The method according to claim 1, characterized in that, before starting the freezing process, the oocytes are exposed to the second solution for a time of 13–15 min.

8. The method according to claim 1, characterized in that said oocytes are fresh human ooccytes.

* * * * *

UNITED STATES PATENT AND TRADEMARK OFFICE
CERTIFICATE OF CORRECTION

PATENT NO. : 7,011,937 B2
DATED : March 14, 2006
INVENTOR(S) : Raffaella Fabbri

It is certified that error appears in the above-identified patent and that said Letters Patent is hereby corrected as shown below:

Column 1,
Line 31, "congesting" should read -- contrasting --.
Line 62, "ad" should read -- and --.

Column 2,
Line 12, "face" should read -- fact --
Line 14, "highly" should read -- the cell --.

Column 3,
Line 22, "prepares" should read -- prepare --.

Column 4,
Line 12, "(92%) of fresh human oocytes" should read -- (82%) of fresh human oocytes --.
Line 42, "tat" should read -- that --.

Signed and Sealed this

Thirteenth Day of June, 2006

JON W. DUDAS
*Director of the United States Patent and Trademark Office*